United States Patent [19]

Weeks

[11] Plant 4,736

[45] Jun. 9, 1981

[54] ROSE PLANT

[76] Inventor: O. L. Weeks, 4759 Philadelphia St., Chino, Calif. 91710

[21] Appl. No.: 151,474

[22] Filed: May 16, 1980

[51] Int. Cl.[3] ..... A01H 5/00

[52] U.S. Cl. ..... Plt./11

[58] Field of Search ..... Plt./11

*Primary Examiner*—Robert E. Bagwill
*Attorney, Agent, or Firm*—Vincent G. Gioia

[57] ABSTRACT

A new hybrid tea rose variety of carrot red coloring but which may contain peach and dark orange tones.

1 Drawing Figure

The present invention relates to a new and distinct variety of rose plant of the hybrid tea rose class, which was originated by my crossing as seed parent the rose known as "Tanya" and the rose known as "Jack O'Lantern" as pollen parent.

Among the novel characteristics possessed by this new variety which distinguish it from its parents and all other varieties of which I am aware are orange colored buds first opening into orange colored flowers with varied shading and developing into carrot red blooms. An upright, bushy free branching plant with abundant foliage and superior disease resistance. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine hybrid tea rose blooming singly and in irregular clusters of up to several blooms. The flowers are of good petalage and hold well.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "31C" is plate 31C of the Royal Horticultural Society Color Chart.

Parentage: Seedling.
*Seed parent.*—"Tanya".
*Pollen parent.*—"Jack O'Lantern".
Class: Hybrid tea.

The following observations are made of specimens grown outdors in San Bernardino County, Calif., during the month of October.

1. FLOWER

Blooming habit: Intermittent to continuous.

A. Bud:
- (1) *Size.*—Medium.
- (2) *Form.*—Pointed, ovoid.
- (3) *Color.*—When sepals first divide and petals begin to unfurl: Predominant bud color as seen on undersurface of outer petals is Mars orange 31C (with some deeper tonality of petal tip) and top surface, seen upon unfurling, is tangerine orange 24C to nasturtium orange 25D. As more petals unfurl, the varied shading of the upper surface of individual petals from deeper tones toward point of petal attachment to lighter shades (27C) toward petal edge, is seen.
- (4) *Sepals.*—Longer than bud, with foliaceous appendages, recurved.
- (5) *Peduncle.*—Length — long. Aspect — straight, with prickles. Strength — erect. Color — reddish green shading to green.

B. Bloom:
- (1) *Size.*—Average size when fully expanded — about 3 to 5 inches.
- (2) *Borne.*—Singly and in irregular clusters of up to several blooms.
- (3) *Form.*—Relatively high centered slightly flaring, petals quill to points.
- (4) *Petalage.*—Number of petals under normal conditions — about 30 to 34.
- (5) *Color.*—As buds unfurl, deeper orange color tones of the undersurface of the outer petals becomes less visible and there is color contrast between the top and undersurface of central and inner petals. General tonality of the ½ to full open bloom is carrot red 29C, however, lighter peach tones 29D and darker orange tones 31D may also be seen. In ⅓ to ½ open stage more of the color contrast between top and undersurface petal coloring is seen with varied coloring ranging light color 27C through peach 29D, nasturtium orange 25D approaching carrot red 29B.

C. Petals:
- (1) *Texture.*—Moderately thick.
- (2) *Appearance.*—Satiny.
- (3) *Form.*—Rounded with curved petal edge that roll under (quill) to point.
- (4) *Arrangement.*—Regularly arranged.
- (5) *Petaloids in center.*—Many.
- (6) *Persistence.*—Drop off cleanly.
- (7) *Fragrance.*—Slight.
- (8) *Lasting quality.*—Long lasting on plant and as cut flower.

2. REPRODUCTIVE ORGANS

A. Stamens, filaments and anthers:
- (1) *Arrangement.*—Many, irregularly arranged.
- (2) *Color.*—Yellow.

B. Pollen: Color — abundant, yellow.

C. Styles: Uneven, columnar.

D. Stigmas: Color — reddish yellow.
E. Hips: Nonobserved.

3. PLANT

A. Form: Upright, bushy.
B. Growth: Moderately vigorous, free branching.
C. Foliage: Compound 3 to 5 leaflets.
(1) *Size.*—Medium.
(2) *Quantity.*—Abundant.
(3) *Color.*—New foliage: Purplish shading to purplish green and then becoming 147A. Old foliage: Upper side — near to 139A. Under side — near to 191B.
(4) *Shape.*—Elliptical.
(5) *Texture.*—Glossy, leathery.
(6) *Edge.*—Serrated.
(7) *Serration.*—Simple.
(8) *Leaf stem.*—Color — near to 191B.
(9) *Stipules.*—Long.
(10) *Resistance to disease.*—Blackspot — excellent. Mildew — excellent. Rust — excellent.

D. Wood:
(1) *New wood.*—Color — purplish shading to purplish green and then to 147D. Bark — smooth, shiny.
(2) *Old wood.*—Color — near 137A. Bark — smooth, shiny.
E. Thorns:
(1) *Thorns.*—Quantity (main stalk): ordinary. Form — recurved. Length — medium. Color — reddish bronze to tan. Position — scattered.
(2) *Prickles.*—Few.
F. Winter hardiness: Good winter hardiness.

I claim:

1. A new and distinct variety of rose plant of the hybrid tea class, substantially as shown and described, characterized particularly by multi-orange toned flowers developing into open blooms of more general carrot red tonality borne primarily singly to a stem and which are long lasting on the plant and as cut flowers.

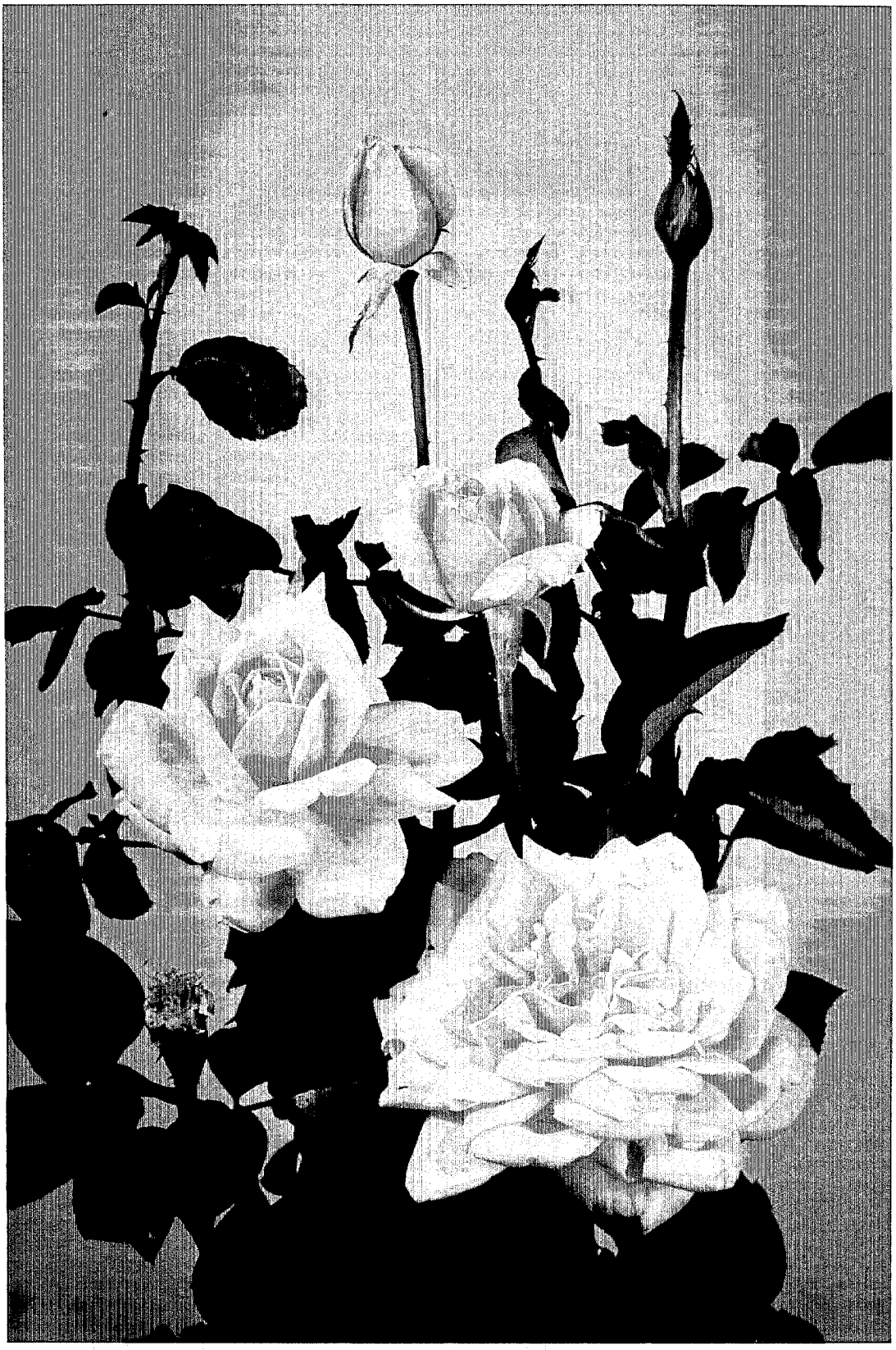

* * * * *